United States Patent [19]

Feder

[11] Patent Number: 5,140,061

[45] Date of Patent: Aug. 18, 1992

[54] AQUEOUS SILICONE DISPERSIONS COMPRISED OF AMINOSILANES/AMIDOSILANES AND CROSSLINKABLE INTO ELASTOMERIC STATE

[75] Inventor: Michel Feder, Illfurth, France

[73] Assignee: Rhone-Poulenc Chimie, Courbevoie, France

[21] Appl. No.: 475,256

[22] Filed: Feb. 5, 1990

[30] Foreign Application Priority Data

Feb. 3, 1989 [FR] France ................ 89 01654

[51] Int. Cl.⁵ .................................. C08K 3/10
[52] U.S. Cl. ........................... 524/783; 524/860; 524/869; 524/786; 524/788; 524/791; 524/785; 524/787; 524/838; 524/864; 528/38; 528/33; 528/10; 428/447; 428/455
[58] Field of Search ............ 524/860, 869, 786, 788, 524/791, 783, 785, 787, 864, 838; 528/11, 38, 33; 428/447, 455

[56] References Cited

U.S. PATENT DOCUMENTS

| | | | |
|---|---|---|---|
| 2,676,182 | 4/1954 | Daudt et al. | 524/860 |
| 2,891,920 | 6/1959 | Hyde et al. | 260/29.2 |
| 3,294,725 | 12/1966 | Findlay et al. | 260/29.2 |
| 3,355,406 | 11/1967 | Cekada, Jr. | 260/29.2 |
| 3,360,491 | 12/1967 | Axon | 260/29.2 |
| 3,364,160 | 1/1968 | Golitz et al. | 260/18 |
| 3,697,469 | 10/1972 | Ikoma | 260/29.2 M |
| 3,706,695 | 12/1972 | Huebner et al. | 427/58 |
| 3,779,967 | 12/1973 | Camp | 260/29.2 M |
| 3,862,919 | 1/1975 | Nitsche et al. | 260/185 |
| 3,925,242 | 10/1975 | Sagi et al. | 252/321 |
| 4,028,339 | 6/1977 | Merrill | 260/46.5 R |
| 4,052,331 | 10/1977 | Dumoulin | 252/312 |
| 4,056,492 | 11/1977 | Merrill | 260/185 |
| 4,152,343 | 5/1979 | Wohlfarth et al. | 260/429.7 |
| 4,221,688 | 9/1980 | Johnson et al. | 260/29.2 M |
| 4,244,849 | 1/1981 | Saam | 260/29.2 M |
| 4,322,518 | 3/1982 | Blizzard | 528/33 |
| 4,496,687 | 1/1985 | Okada et al. | 524/838 |
| 4,525,502 | 6/1985 | Traver | 524/96 |
| 4,535,109 | 8/1985 | Kondo et al. | 524/838 |
| 4,554,187 | 11/1985 | Grape et al. | 427/387 |
| 4,608,412 | 8/1986 | Freiberg | 524/724 |
| 4,618,642 | 10/1986 | Schoenherr | 524/425 |
| 4,618,645 | 10/1986 | Bauman et al. | 524/745 |
| 4,624,900 | 11/1986 | Fau | 428/447 |
| 4,717,599 | 1/1988 | Merrill | 427/387 |
| 4,749,766 | 6/1988 | Millet | 528/18 |
| 4,978,710 | 12/1990 | Liles | 524/837 |

FOREIGN PATENT DOCUMENTS

| | | |
|---|---|---|
| 0143541 | 6/1985 | European Pat. Off. . |
| 147323 | 7/1985 | European Pat. Off. . |
| 169098 | 1/1986 | European Pat. Off. . |
| 0201284 | 11/1986 | European Pat. Off. . |
| 212827 | 3/1987 | European Pat. Off. . |
| 235049 | 9/1987 | European Pat. Off. . |
| 1248826 | 11/1960 | France . |
| 1423477 | 11/1965 | France . |
| 2064563 | 7/1971 | France . |
| 2094322 | 2/1972 | France . |
| 2110358 | 6/1972 | France . |
| 2114230 | 6/1972 | France . |
| 2195655 | 3/1974 | France . |
| 2463163 | 2/1981 | France . |
| 1289900 | 9/1972 | United Kingdom . |
| 1336195 | 10/1973 | United Kingdom . |
| 2056473 | 3/1981 | United Kingdom . |
| WO88/09923 | 12/1988 | World Int. Prop. O. . |

OTHER PUBLICATIONS

Noll, *Chemistry and Technology of Silicones*, Academic Press, p. 337 (1968).

Primary Examiner—John C. Bleutge
Assistant Examiner—Karen A. Hellender
Attorney, Agent, or Firm—Burns, Doane, Swecker & Mathis

[57] ABSTRACT

Aqueous silicone dispersions crosslinkable into elastomeric state upon removal of water therefrom, well adapted for the production of paints and silicone elastomer seals, e.g., for the construction industry, include:

(A) 100 parts by weight of an oil-in-water emulsion of an α,ω-(dihydroxy)polydiorganosiloxane, stabilized with an anionic and/or nonionic surfactant;

(B) 0.1 to 20 parts by weight of an aminosilane and/or amidosilane;

(C) 0 to 3 parts by weight of a metal curing catalyst; and (D) 0 to 250 parts by weight of a non-siliceous inorganic filler, such emulsion having a pH of from 7 to 13 and a dry solids content of at least 40%.

18 Claims, No Drawings

AQUEOUS SILICONE DISPERSIONS COMPRISED OF AMINOSILANES/AMIDOSILANES AND CROSSLINKABLE INTO ELASTOMERIC STATE

BACKGROUND OF THE INVENTION

1. Field of the Invention

The present invention relates to novel aqueous silicone dispersions based on an aminosilane and/or amidosilane, and, more especially, to such novel dispersions that are crosslinkable into elastomeric state upon removal of water therefrom.

2. Description of the Prior Art

U.S. Pat. No. 2,891,920 describes a process for emulsion polymerization of polydiorganosiloxane using an acidic or basic catalyst in the presence of anionic, cationic or nonionic surfactants. This '920 patent suggests that the emulsions obtained are stable on storage and are useful, after addition of fillers, for formulating paints which provide a continuous coating on removal of water therefrom.

U.S. Pat. No. 3,294,725 describes in particular, the use of dodecylbenzenesulfonic acid for the emulsion polymerization of polydiorganosiloxanes. This '725 patent offers that, to produce stable emulsions, it is desirable to adjust the pH of such emulsions to a value of approximately 7. It also relates that an elastomer coating may be produced from these neutralized emulsions to which colloidal silica and a polyalkoxysilane have been added.

The description of U.S. Pat. No. 3,360,491 is similar to that of U.S. Pat. No. 3,294,725, except that the dodecylbenzenesulfonic acid is replaced by lauryl hydrogen sulfate.

U.S. Pat. No. 3,697,469 describes a special process for emulsion polymerization of polydiorganosiloxanes, and notes the possibility of adding colloidal silica and a tin salt to the emulsion for the purpose of producing an elastomer coating upon evaporation of water therefrom.

French Patent FR-A-2,110,358 describes a silicone emulsion having a pH of from 6.5 to 9, which crosslinks into an electrically conducting elastomer after evaporation of water, on incorporation of carbon black therein. The emulsion additionally contains a tin salt and a polyalkoxysilane, is not stable on storage, and must be stored in two separate packs (two-component emulsion).

U.S. Pat. Nos. 4,221,688 and 4,244,849 and French Patent FR-A-2,463,163 describe storage-stable silicone emulsions which contain:

(i) an anionically stabilized emulsion of an $\alpha,\omega$-(dihydroxy)polydiorganosiloxane polymer;
(ii) a siliceous filler;
(iii) a tin salt; and
(iv) optionally, a non-reinforcing filler.

The siliceous filler can be a colloidal silica (U.S. Pat. No. 4,221,688), sodium silicate (U.S. Pat. No. 4,244,849) or an amorphous powdered silica (FR-A-2,463,163).

With respect to the known aqueous emulsions (dispersions) of the prior art, these three patents describe that, on the one hand, to obtain a one-component emulsion stable on storage, the emulsion must be stored at an alkaline pH above 8.5 or 9, and preferably above 10, and, on the other hand, that a tin salt should be incorporated in the emulsion in order to shorten to a few days the stage of maturation of the emulsion necessary for producing a dispersion capable of crosslinking.

U.S. Pat. No. 3,355,406 describes a silicone latex including an $\alpha,\omega$-(dihydroxy)polydiorganosiloxane, preferably prepared by emulsion polymerization, and a silsesquioxane resin comprising $RSiO_{1.5}$ units (R=hydrocarbon residue). The latex can contain, in addition, a metal curing catalyst and an alkyltrialkoxysilane.

In U.S. Pat. No. 4,554,187, the silicone resin combined with the $\alpha,\omega$-(dihydroxy)polydiorganosiloxane is a low molecular weight reactive resin having alkoxy or acyloxy groups.

In Patent Application EP-A-366,729, the silicone resin combined with the $\alpha,\omega$-(dihydroxy)polydiorganosiloxane and the curing catalyst is a siliconate.

A silicone resin containing up to 10% by weight of hydroxyl groups may be combined with this siliconate.

U.S. Pat. No. 4,618,642 describes an aqueous silicone dispersion containing a non-siliceous filler and an alkoxysilane or a ketiminoxysilane. According to U.S. Pat. No. 4,608,412, an alkyl orthosilicate is also useful. The aqueous dispersions obtained possess, however, insufficient storage stability.

The use of an alkoxysilane combined with a siliceous filler is, moreover, described in U.S. Pat. No. 4,618,645.

Aminosilanes and amidosilanes are known compounds, the combination of which, protected from atmospheric moisture, with an $\alpha,\omega$-(dihydroxy)diorganopolysiloxane and a curing catalyst, provides a one-component composition stable on storage in the absence of water and crosslinking into an elastomer in the presence of atmospheric moisture, as described, for example, in FR-A-1,248,826 and FR-A-1,423,477.

However, these two patents neither describe nor suggest that the silicone composition can be in the form of an aqueous dispersion.

Furthermore, the prior art relating to aqueous silicone dispersions does not describe the use of aminosilane and/or amidosilanes in combination with an aqueous emulsion of an $\alpha,\omega$-(dihydroxy)diorganopolysiloxane and, optionally, a metal curing catalyst.

SUMMARY OF THE INVENTION

Accordingly, a major object of the present invention is the provision of novel aqueous silicone dispersions which are stable on storage for several months and which crosslink properly and sufficiently rapidly into an elastomer upon removal of water therefrom at ambient temperature, the elastomer formed retains its mechanical properties during aging.

Another object of the present invention is the provision of novel aqueous silicone dispersions of the above type, the maturation stage of which may be effected at low temperatures (20° to 60° C.) and during a period of time of less than 48 hours.

Another object of this invention is the provision of novel aqueous silicone dispersions of the above type which can contain, in addition to inert fillers, basic fillers and acidic fillers.

Still another object of this invention is the provision of novel aqueous silicone dispersion of the above type crosslinkable into elastomers possessing, in addition, improved flame resistance.

Yet another object of the present invention is the provision of novel aqueous silicone dispersions of the above type crosslinkable into elastomers which display satisfactory adhesion to a variety of supports and substrates, especially to glass, concrete and metals (steel, aluminum).

Briefly, the present invention features aqueous silicone dispersions crosslinkable into elastomeric state upon removal of water therefrom under ambient conditions and which comprise:

(A) 100 parts by weight of an oil-in-water emulsion of an α,ω-(dihydroxy)polydiorganosiloxane, stabilized with at least one anionic or nonionic surfactant or mixture thereof;

(B) 0.1 to 20 parts by weight of a silane of the formula:

in which X is a hydrolyzable group selected from an amino and an amido radical; $R_1$ is a monovalent $C_1$–$C_{13}$ hydrocarbon radical; $R_2$ is a $C_1$–$C_8$ aliphatic organic radical selected from among alkyl radicals, alkyl ether radicals, alkyl ester radicals and cyanoalkyl radicals or a $C_7$–$C_{13}$ aralkyl radical; a is an integer equal to 2, 3 or 4; b is an integer equal to 0 or 1; and a+b is equal to 2, 3 or 4;

(C) 0 to 3 parts by weight of a catalytic metal curing compound;

(D) 0 to 250 parts by weight of a non-siliceous inorganic filler, said dispersion having a pH above 7, and preferably ranging from 8 to 13, and a dry solids content of at least 40%.

DETAILED DESCRIPTION OF THE PREFERRED EMBODIMENTS OF THE INVENTION

More particularly according to the present invention, the α,ω-(dihydroxy)polydiorganosiloxanes should have a viscosity of at least 100 mPa.s at 25° C., and preferably at least 50,000 mPa.s.

Indeed, elastomers are produced from polymers having viscosities of above 50,000 mPa.s that possess a suitable combination of mechanical properties, especially in respect to Shore A hardness and elongation.

Furthermore, the higher the viscosity, the better the mechanical properties are retained during aging of the elastomer.

The preferred viscosities according to the present invention range from 50,000 to 1,500,000 mPa.s at 25° C.

The organic radicals of the α,ω-(dihydroxy)polydiorganopolysiloxanes are monovalent hydrocarbon radicals containing up to 6 carbon atoms, optionally substituted with cyano or fluoro groups. Because of their availability in industrial products, the substituents generally used are methyl, ethyl, propyl, phenyl, vinyl and 3,3,3-trifluoropropyl radicals. In general, at least 80% of the number of such radicals are methyl radicals.

According to the present invention, it is more especially preferred to use α,ω-(dihydroxy)polydiorganosiloxanes prepared by the anionic polymerization process described in the above U. S. patents, namely, U.S. Pat. No. 2,891,920 and most especially U.S. Pat. No. 3,294,725. The polymer obtained is anionically stabilized with a surfactant which according to U.S. Pat. No. 3,294,725, is preferably an alkali metal salt of an aromatic hydrocarbon-based sulfonic acid, the free acid also serving as a polymerization catalyst.

The preferred catalyst and surfactant are dodecylbenzenesulfonic acid and its alkali metal salts, especially its sodium salt. Other anionic or nonionic surfactants may optionally be added. However, this addition is unnecessary since, as per U.S. Pat. No. 3,294,725, the amount of anionic surfactant resulting from neutralization of the sulfonic acid is sufficient to stabilize the polymer emulsion. This amount is generally less than 3%, and preferably 1.5%, of the weight of the emulsion.

Such emulsion polymerization process is especially advantageous, since it enables the emulsion (A) to be obtained directly. Moreover, this process makes it possible for α,ω-(dihydroxy)polydiorganosiloxane emulsions (A) of very high viscosity to be produced without difficulty.

To prepare the emulsion (A), an already polymerized α,ω-(dihydroxy)polydiorganosiloxane can also be used, which is than converted into an aqueous emulsion, and the emulsion stabilized with an anionic and/or nonionic surfactant according to a process well-known to this art and abundantly described in the literature (see, for example, FR-A-2,064,563, FR-A-2,094,322, FR-A-2,114,230 and EP-A-169,098).

According to this process, the α,ω-(dihydroxy)-polydiorganosiloxane polymers are mixed by simple stirring with the anionic or nonionic surfactant, it being possible for the latter to be in aqueous solution, water is then added, if necessary, and the mixture is converted into a fine and homogeneous emulsion by passing same through a conventional colloid mill.

The resulting milled preparation is subsequently diluted with a suitable amount of water and an emulsion (A), stabilized with an anionic or nonionic surfactant and stable on storage, is thereby produced.

The amount of anionic and nonionic surfactant incorporated is that commonly used for conducting the emulsification process, especially the processes described in the aforementioned patents and in U.S. Pat. No. 2,891,920.

According to the present invention, the preferred anionic surfactants are alkali metal salts of an aromatic hydrocarbon-based sulfonic acid, and the preferred nonionic surfactants are polyoxyethylenated alkylphenols. These nonionic surfactants are of course the same as those which can optionally be added to the emulsions (A) produced by emulsion polymerization, as indicated above.

The emulsion (A), prepared by emulsion polymerization or by emulsification of the silicone polymer, is in the form of an oil-in-water emulsion, and preferably has a dry solids content of more than 45% by weight.

From 0.1 to 20 parts by weight, and preferably from 0.5 to 10 parts by weight, of silane (B) of formula (1) is/are incorporated per 100 parts by weight of emulsion (A).

The radicals X of the silanes of formula (1) include, more especially, amino radicals of the formula:

wherein $R_3$ is preferably a $C_1$–$C_6$ alkyl radical, a phenyl radical or a cyclohexyl radical.

These aminosilanes are, in particular, described in the aforementioned FR-A-1,248,826.

The amidosilanes are, in particular, described in the aforementioned FR-A-1,423,477.

The radicals X of the silanes of formula (1) include, more especially, amido radicals of the formula:

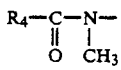

wherein $R_4$ is preferably a $C_1$-$C_6$ alkyl radical or a phenyl radical.

The radicals $R_1$ of the formula (1) include alkyl and alkenyl radicals such as methyl, ethyl, propyl, vinyl, allyl, 3,3,3-trifluoropropyl and cyanoethyl, aryl radicals such as phenyl and cycloalkyl radicals such as cyclohexyl.

The radicals $R_2$ of the formula (1) include $C_1$-$C_8$ alkyl radicals such as methyl, ethyl, propyl and 2-ethylhexyl, aralkyl radicals such as benzyl, alkyl ether radicals such as 2-methoxyethyl, cyanoalkyl radicals such as 2-cyanoethyl and alkyl ester radicals such as the 2-acetoxyethyl radical.

In the formula (1), the radicals $R_1$, $R_2$, $R_3$, $R_4$ and $R_5$ may be identical or different.

Exemplary of the aminosilanes, the following are representative:
Methyltris(n-butylamino)silane;
Methyltris(2-ethylhexylamino)silane;
Phenyltris(isobutylamino)silane;
Methyltris(cyclohexylamino)silane;
Phenyltris(ethylamino)silane;
Methylmethoxybis(N-methylamino)silane;
Tetra(N,N-diethylamino)silane; and
Methyltris(phenylamino)silane.

Exemplary of the amidosilanes, the following are representative:
Methyltris(N-methylacetamido)silane;
Methyltris(N-methylbenzamido)silane;
Methylmethoxybis(N-methylacetamido)silane; and
Methylethoxybis(N-methylbenzylamino)silane.

The silanes (B) and their products of partial hydrolysis serve as crosslinking agents in the aqueous silicone dispersions according to the invention.

The catalytic metal curing compounds (C) are not required, most especially if certain basic fillers (D) mentioned below are used. However, these catalysts enable the maturation of the system to be accelerated considerably. Useful catalysts include the carboxylic acid salts and halides of metals selected from among lead, zinc, zirconium, titanium, iron, tin, barium, calcium and manganese.

The constituent (C) is preferably a catalytic tin compound, typically an organotin salt, preferably introduced in the form of an aqueous emulsion. Useful organotin salts are described, in particular, in the text by Noll, *Chemistry and Technology of Silicones*, Academic Press, page 337 (1968).

It is also possible to use, as a catalytic tin compound, the reaction product of a tin salt, especially a tin dicarboxylate, with poly(ethyl silicate), as described in U.S. Pat. No. 3,862,919.

It is possible to use the reaction product of an alkyl silicate or an alkyltrialkoxysilane with dibutyltin diacetate, as described in Belgian Patent BE-A-842,305.

The preferred tin salts are tin bischelates (EP-A-147,323 and EP-A-235,049), diorganotin dicarboxylates, and especially dibutyl- or dioctyltin diversatates (British Patent GB-A-1,289,900), dibutyl- or dioctyltin diacetate and dibutyl- or dioctyltin dilaurate. From 0.01 to 3 parts by weight, and preferably from 0.05 to 2 parts by weight, of organotin salt is/are preferably used per 100 parts by weight of (A).

Another constituent of the dispersion according to the invention is 0 to 250 parts by weight, and preferably from 5 to 200 parts by weight, of a non-siliceous inorganic semi-reinforcing or packing filler (D).

The fillers (D) have a particle size generally ranging from 0.001 to 300 μm and a BET surface area of less than 100 m²/g.

Exemplary of such fillers (D), whether employed alone or in admixture, are carbon black, titantium dioxide, aluminum oxide, hydrated alumina, expanded vermiculite, non-expanded vermiculite, calcium carbonate, zinc carbonate, magnesium carbonate, magnesium oxide, zinc oxide, mica, talc, iron oxide, barium sulfate and slaked lime.

These fillers can substantially accelerate the curing of the dispersion, and can also serve, either wholly or partially, the function of the catalyst (C).

These fillers (D) are introduced into the emulsion (A) in the form of a dry powder, for example by simple blending.

In one embodiment of the invention, it was discovered that, if the filler (D) essentially consists of only a filler selected from hydrated alumina, expanded vermiculite and non-expanded vermiculite, in an amount of from 5 to 250 parts by weight, and preferably from 10 to 200 parts by weight, per 100 parts by weight of emulsion (A), an elastomer is produced having an especially high flame resistance which cannot be attained with the other categories of filler (D) mentioned above, especially with aluminum oxide or unhydrated alumina. It is also possible to incorporate ceramic or aramid fibers, as per EP-A-212,827.

In another embodiment of the invention, it is possible to incorporate, in addition, per 100 parts by weight of emulsion (A), a silicon-containing additive (E) selected from sodium silicate (0.3 to 30 parts by weight) and a siliceous reinforcing or semi-reinforcing filler (1 to 150 parts by weight).

Such siliceous fillers include colloidal silica and pyrogenic and precipitated silica powders, or a mixture thereof. Pyrogenic silica is preferred. It is, however, also possible to use siliceous semi-reinforcing fillers such as diatomaceous earths and ground quartz.

The sum of the parts by weight of (D)+(E) must be less than 300 parts by weight per 100 parts by weight of emulsion (A).

Pyrogenic and precipitated silica powders are well known to this art; they are used, in particular, as fillers in hot-vulcanizing silicone elastomer compositions and silicone rubber. These powders have a mean particle size generally of less than 0.1 μm, and a BET specific surface area of more than 50 m²/g, and preferably ranging from 150 to 350 m²/g.

The incorporation of this silicon-containing additive (E) in the emulsion (A), by any suitable means, especially by stirring, considerably increases the viscosity of the emulsion (A), which then becomes pasty in nature.

Thus, it has now been determined according to the present invention that the addition of this silicon-containing additive (E) is sufficient to impart to the dispersion a more or less pronounced "thixotropic" character. The emulsion, extracted, for example, from a storage package, adheres even to a vertical substrate without flowing, and cures into an elastomer upon evaporation of water therefrom at ambient temperature. It is also possible to obtain a non-flowing emulsion using as a filler (D) calcium carbonate having a mean particle diameter of less than 0.1 μm. Of course, slight heating (to about 40° to 80° C.) of the composition to accelerate the evaporation of water is also within the ambit of the invention.

It is possible to incorporate, in addition, per 100 parts by weight of emulsion (A), from 1 to 40 parts by weight, and preferably from 2 to 20 parts by weight, calculated as dry solids, of an hydroxylated silicone resin (F).

The hydroxylated silica resin (F) has a weight content of hydroxyl groups ranging from 0.1% to 10%, and preferably from 1% to 6%.

This resin (F) comprises, per molecule, at least two different recurring units selected from among those of the following formulae: $R_3Si)_{0.5}$ (unit M), $R_2SiO$ (unit D), $RSiO_{1.5}$ (unit T) and $SiO_2$ (unit Q).

The units M, D, T and Q are distributed in such manner that the mole ratio R/Si is less than 2, and preferably less than 1.8, as to exclude linear polydiorganosiloxanes.

The radicals R, which may be identical or different, are vinyl, phenyl and 3,3,3-trifluoropropyl radicals and linear or branched chain alkyl radicals having from 1 to 6 carbon atoms, inclusive.

Exemplary of the alkyl radicals R are methyl, ethyl, isopropyl, tert-butyl and n-hexyl radicals.

These silicone resins are well-known branched organopolysiloxane polymers, the processes for the preparation of which are described in a very large number of patents.

Exemplary of useful such resins are the MQ resins, MQD resins, TD resins and MDT resins.

It is possible to use resins which are solid or liquid at ambient temperature. These resins may be incorporated in the aqueous emulsions as such, dissolved in an organic solvent or a silicone oil, or alternatively in the form of aqueous emulsions.

Useful aqueous emulsions of such silicone resins are described, for example, in U.S. Pat. Nos. 4,028,339, 4,052,331, 4,056,492, 4,525,502 and 4,717,599.

In a preferred embodiment of the invention, the adhesion of the elastomers derived from the subject dispersions to various supports may be greatly improved by adjusting the pH of the dispersion to a value ranging from 8 to 13 by adding thereto a suitable amount of an aqueous solution of a strong inorganic base (G) selected from among the alkali metal or alkaline earth metal hydroxides, such as sodium hydroxide, potassium hydroxide, calcium hydroxide, magnesium hydroxide and barium hydroxide.

Other additives optionally incorporated into the dispersions according to the invention include the antifreezes, antifungal agents, antifoams and also thixotropic agents such as carboxymethylcellulose, xanthan gum and polyvinyl alcohol.

The dispersions according to the invention are preferably prepared in the following manner:

The starting material is an emulsion (A), prepared either by the emulsion polymerization process, in which case an emulsion stabilized with an anionic and optionally a nonionic surfactant is obtained, or by the process of emulsification of the α,ω-(dihydroxy)polydiorganosiloxane, in which case an emulsion stabilized with an anionic and/or a nonionic surfactant is obtained.

To prepare the dispersions according to the invention, it is recommended to first adjust, at ambient temperature, the pH of the emulsion (A) to a value of from 7 to 13, and preferably from 8 to 13, by means of an organic base (for example diethylamine) or an inorganic base [additive (G)]. The additive (G) is preferred, since it makes it possible to produce an elastomer which adheres better to supports.

The catalyst (C) is added next if appropriate, followed by the silane (B) and optionally the filler (D) and (E), as well as the resin (F).

The resin (F) is added as is, or dissolved in an organic solvent or in a silicone oil, or alternatively in the form of an aqueous emulsion.

A representative silicone oil is a trimethylsilyl-blocked polydimethylsiloxane, having a viscosity at 25° C. of from 100 to 5,000 mPas.

The final emulsion is homogenized and then degassed, and is thereafter packaged in a container sealed against atmospheric oxygen and against water vapor.

The constituents (A), (B) and optionally (C), (D), (E), (F) and (G) are mixed in amounts such that the final emulsion has a dry solids content of more than 40%, preferably more than 60%, but generally less than 90%. The preferred pH range is from 8 to 13.

The dispersions according to the invention may be used as a paint capable of crosslinking into a thin layer. They then preferably have a dry solids content of from 40% to 70%.

To determine the dry solids content, 2 g of dispersion are placed in an aluminum weighing boat, which is heated for one hour to 150° C. in an air circulation oven. After being cooled, the boat is weighed again and the percentage of material remaining from the initial 2 g, which represents the dry solids content, is determined.

In a preferred embodiment of the invention, after preparation thereof, the dispersion is subjected to a maturation stage, at ambient temperature, ranging from a few hours to a few days.

This maturation stage simply entails permitting the dispersion to stand protected from atmospheric oxygen before its use.

The dispersions according to the invention may be used for the production of silicone elastomer seals, especially for the construction industry.

These dispersions are also useful for coating various pharmaceutical or plant-protection active principles formulated in solid form (pellets, tablets, pills, and the like), for the coating of cork stoppers used for sealing bottles of wines and spirits, and for producing coatings on kitchenware and, generally speaking, on articles in contact with foodstuffs (for example bread tins).

Known coating techniques are applicable for such purpose, especially brush and dip (immersion) coating techniques, spray techniques, fluidized bed coating techniques and immersion coating techniques.

For coatings on cork stoppers, one recommended technique is the dip coating technique which entails immersing the stoppers in the dispersion which wets the surface of the stopper, and then evaporating the water therefrom.

The coating obtained represents 20 to 50 mg of elastomer per 100 cm² of stopper surface. This layer facilitates the sliding of the stopper into the neck of the bottle during bottling, and avoids "runs", namely, leakages of liquid between the neck and the stopper.

In order to further illustrate the present invention and the advantages thereof, the following specific examples are given, it being understood that same are intended only as illustrative and in nowise limitative. In said examples to follow, all parts and percentages are given by weight.

EXAMPLE 1

Preparation of the emulsion (A)

The emulsion (A) was obtained by emulsion polymerization of α,ω-(dihydroxy)polydimethylsiloxane oil having a viscosity of 100 mPa.s at 25° C. in the presence of dodecylbenzenesulfonic acid.

When the viscosity of the oil reached $10^6$ mPa.s at 25° C., the polymerization was stopped by neutralization of the catalyst.

The resulting emulsion (A) had a dry solids content of 59%.

To 100 parts of emulsion (A), 2.2 parts of 30% strength aqueous potassium hydroxide solution (G) and then 1.5 parts of aqueous emulsion (C) containing 37% by weight of di-n-octyltin dilaurate, 4.1 parts of methylethoxybis(N-methylbenzylamino)silane (B) and 58.5 parts of precipitated $CaCO_3$ powder (D) of mean particle size 70 nanometers were added under stirring.

The constituents (A), (B), (C), (D) and (G) were added in the order stated at ambient temperature, and observing an incorporation time of approximately 15 minutes for each reactant.

The final dispersion had a dry solids content of 70% and possessed a natural pH of 9.

The final dispersion was homogenized for 30 minutes under vacuum and then packaged in a container sealed against atmospheric oxygen and against water vapor.

After 7 days of storage, the dispersion was spread with a scraper in a layer (film) 2 mm thick, which was permitted to dry for 7 days at ambient temperature (20° C.) in the case of a first batch and for 3 months at ambient temperature in the case of a second batch.

The appearance, extrusion and reactivity of the dispersions were modified to only a very slight extent after 3 months of storage.

The following average mechanical properties were measured in the dried films:

(i) Shore A hardness (SAH) according to standard ASTM-D-2240;
(ii) the rupture strength (RS) according to standard AFNORT-T 46,002 corresponding to standard ASTMSD 412, in MPa.s;
(iii) the elongation at rupture (E/R) in % according to standard AFNOR-T 46,002;
(iv) the modulus of elasticity (ME) at 100% elongation according to standard AFNOR-T 46,002, in MPa.

The mechanical properties obtained are reported in the Table below.

To assess adhesion, one ribbon of aqueous dispersion 4 mm thick was deposited onto a glass or concrete support. After 12 days, the adhesion of the elastomer formed was assessed by manually pulling the ribbon.

Adhesion was designated in three ways:
(a) good adhesion, when the ribbon cannot be detached from its support (designated ++);
(b) moderate adhesion, when the ribbon is detached with difficulty and is stripped over small areas (designated +);
(e) lack of adhesion, when the ribbon detached easily (designated 0).

The mechanical properties and assessments of adhesion are reported in the Table below.

EXAMPLE 2

The procedure of Example 1 was repeated exactly, except that 4.1 parts of methyltris(cyclohexylamino)silane were added in place of the 4.1 parts of benzamidosilane.

The pH of the final dispersion was 9.

The final emulsion had a dry solids content of 71%.

The mechanical properties and assessments of adhesion are reported in the Table below.

TABLE

|  |  | EXAMPLE 1 | EXAMPLE 2 |
|---|---|---|---|
| SAH | 7 days at 20° C. | 30 | 20 |
|  | 3 months at 20° C. | 27 | 18 |
| RS (MPa) | 7 days at 20° C. | 1.05 | 0.9 |
|  | 3 months at 20° C. | 1.00 | 0.7 |
| E/R (%) | 7 days at 20° C. | 468 | 713 |
|  | 3 months at 20° C. | 440 | 685 |
| ME (MPa) | 7 days at 20° C. | 0.46 | 0.31 |
|  | 3 months at 20° C. | 0.44 | 0.30 |
| ADHESION GLASS |  | ++ | ++ |
| ADHESION CONCRETE |  | + | + |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An aqueous silicone dispersion crosslinkable into elastomeric state upon removal of water therefrom under ambient conditions, comprising:

(A) 100 parts by weight of an oil-in-water emulsion of an α,ω-(dihydroxy)polydiorganosiloxane, stabilized with at least one anionic or nonionic surfactant, or mixture thereof;

(B) 0.1 to 20 parts by weight of a silane of the formula:

in which X is a hydrolyzable amino or amido radical, in which the N-atom is directly linked to the Si-atom; $R_1$ is a monovalent $C_1$–$C_{13}$ hydrocarbon radical; $R_2$ is a $C_1$–$C_8$ alkyl radical, alkyl ether radical, alkyl ester radical or cyanoalkyl radical, or a $C_7$–$C_{13}$ aralkyl radical; a is an integer equal to 2, 3 or 4; b is an integer equal to 0 to 1; and a+b is equal to 2, 3 or 4;

(C) 0 to 3 parts by weight of a catalytic metal curing compound;

(D) 0 to 250 parts by weight of a non-siliceous inorganic filler; and said dispersion having a pH above 7 and a dry solids content of at least 40%.

2. The aqueous silicone dispersion of claim 1, wherein the amino radicals, X, are of the formula:

and amido radicals are of the formula:

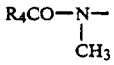

wherein $R_3$ is a $C_1$–$C_6$ alkyl radical, a phenyl radical or a cyclohexyl radical and $R_4$ is a $C_1$–$C_6$ alkyl radical or a phenyl radical.

3. The aqueous silicone dispersion as defined by claim 1, comprising 0.01 to 3 parts of said metal curing compound (C).

4. The aqueous silicone dispersion as defined by claim 2, said metal compound (C) comprising an aqueous emulsion of an organotin salt.

5. The aqueous silicone dispersion as defined by claim 1, said emulsion (A) having a dry solids content of at least 45% by weight.

6. The aqueous silicone dispersion as defined by claim 1, said filler (D) comprising 5 to 200 parts by weight of hydrated alumina, alumina, calcium carbonate, expanded vermiculite, non-expanded vermiculite, carbon black, zinc oxide, titanium dioxide, mica, talc, iron oxide, barium sulfate or slaked lime.

7. The aqueous silicone dispersion as defined by claim 6, said filler (D) comprising calcium carbonate having a mean particle diameter of less than 0.1 $\mu$m.

8. The aqueous silicone dispersion as defined by claim 1, comprising:
(A) 100 parts by weight of an oil-in-water emulsion of an $\alpha,\omega$-(dihydroxy)polydiorganosiloxane having a viscosity at 25° C. of from 50,000 to 1,500,000 mPa.s, such emulsion being stabilized with an alkali metal salt of an aromatic hydrocarbon-based sulfonic acid or polyoxyethylenated alkylphenol surfactant;
(B) 0.5 to 10 parts by weight of silane;
(C) 0.05 to 2 parts by weight of a diorganotin dicarboxylate;
(D) 10 to 20 parts by weight of an inorganic filler; and said emulsion having a pH ranging from 8 to 13 and a dry solids content of at least 60%.

9. The silicone dispersion as defined in claim 1, further comprising, per 100 parts by weight of emulsion (A), 1 to 40 parts by weight of a hydroxylated silicone resin (F) which comprises, per molecule, at least two different recurring units selected from among those of the formulae $R_3SiO_{0.5}$, $R_2SiO$, $RSiO_{1.5}$ and $SiO_2$, wherein the radicals R, which may be identical or different, are vinyl, phenyl or 3,3,3-trifluoropropyl radicals, or linear or branched chain alkyl radicals having from 1 to 6 carbon atoms, said resin (F) having a weight content of hydroxyl groups ranging from 0.1% to 10%.

10. The aqueous silicone dispersion as defined by claim 1, comprising a pH-adjusting amount of an alkali metal or alkaline earth metal hydroxide.

11. The aqueous silicone dispersion as defined by claim 1, in crosslinked elastomeric state.

12. A substrate article coated with the aqueous silicone dispersion as defined by claim 1.

13. A substrate article coated with the elastomer as defined by claim 11.

14. The substrate article as defined by claim 12, comprising a coated pharmaceutical or agricultural chemical.

15. The substrate article as defined by claim 12, comprising a bottle cork.

16. A shaped article comprising the elastomer as defined by claim 11.

17. The aqueous silicone dispersion as defined by claim 1, further comprising:
(E) a silicon-containing additive selected from sodium silicate (0.3 to 30 parts by weight) and a siliceous reinforcing or semi-reinforcing filler (1 to 150 parts by weight).

18. The aqueous silicone dispersion as defined by claim 17, further comprising, per 100 parts by weights of the emulsion (A), 0.3 to 30 parts by weight of sodium silicate and 100 to 150 parts by weight of a siliceous reinforcing or semi-reinforcing filler, with the proviso that the sum of the parts by weight of (D)+(E) is less than 300 parts by weight per 100 parts by weight of (A).

* * * * *